United States Patent [19]

Fozzard

[11] 4,117,001
[45] Sep. 26, 1978

[54] PYROLYSIS OF HEAVIES FORMED IN PRODUCTION OF UNSATURATED DINITRILES

[75] Inventor: George B. Fozzard, Bartlesville, Okla.

[73] Assignee: Phillips Petroleum Company, Bartlesville, Okla.

[21] Appl. No.: 813,063

[22] Filed: Jul. 5, 1977

[51] Int. Cl.$^2$ .................. C07C 120/00; C07C 121/20; C07C 121/70
[52] U.S. Cl. .............................. 260/465.8 R; 260/464; 260/465 H; 260/465.3; 260/465.9
[58] Field of Search ................ 260/465.9, 464, 465 K, 260/465.8 R, 465 H

[56] References Cited

U.S. PATENT DOCUMENTS

| | | | |
|---|---|---|---|
| 2,407,848 | 9/1946 | Ray | 260/465.9 |
| 2,641,607 | 6/1953 | Albisetti et al. | 260/465.9 |
| 3,247,237 | 4/1966 | Hagemeyer, Jr. | 260/465.9 |
| 3,840,583 | 10/1974 | Turk et al. | 260/465.8 R |
| 3,898,268 | 8/1975 | Drake | 260/464 X |
| 3,929,860 | 12/1975 | Drake | 260/464 X |
| 3,985,786 | 10/1976 | Drake | 260/465.8 R |
| 3,996,262 | 12/1976 | Turk et al. | 260/464 X |
| 4,001,294 | 1/1977 | Drake et al. | 260/465.8 R |
| 4,021,465 | 5/1977 | Fozzard et al. | 260/465.8 R |

OTHER PUBLICATIONS

Burlant et al., J. Polymer Science, vol. XVII, pp. 249-256, (1956).
Brandrup et al., Polymer Handbook, Interscience, (1966), pp. V-5-V-11.

*Primary Examiner*—Joseph Paul Brust

[57] ABSTRACT

An olefinically unsaturated mononitrile is reacted with a monadduct of an olefinically unsaturated mononitrile and an olefinically unsaturated hydrocarbon compound to produce a dinitrile product and undesired compounds having higher boiling points than the dinitrile product. The undesired compounds are separated from the dinitrile product and subjected to distillation to produce a light cut and a heavy cut thereof. The light cut is then subjected to pyrolysis conditions to decompose at least a portion thereof to olefinically unsaturated mononitrile, olefinically unsaturated hydrocarbon compound, and monadduct, which can be recovered and recycled to the dinitrile synthesis.

31 Claims, 1 Drawing Figure

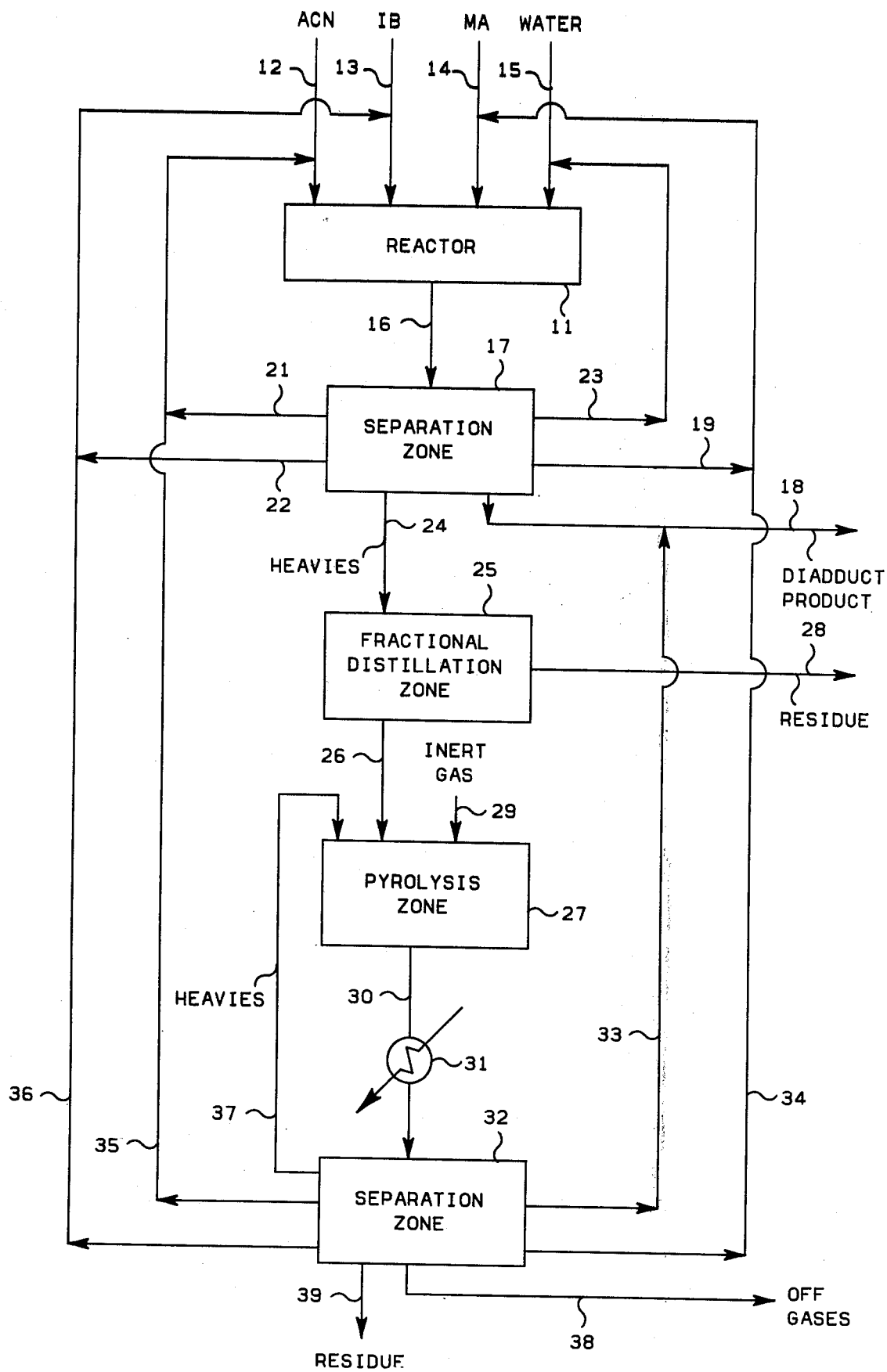

PYROLYSIS OF HEAVIES FORMED IN PRODUCTION OF UNSATURATED DINITRILES

This invention relates to the production of unsaturated dinitriles. In a specific aspect the invention relates to the pyrolysis of the undesirable heavy byproducts or heavies to recover starting materials.

U.S. Pat. NO. 3,840,583 of S. D. Turk and C. A. Drake describes the preparation of olefinically unsaturated dinitriles (diadduct) from an olefin, an unsaturated mononitrile, and a monoadduct reaction product of the olefin and the mononitrile. In particular, the use of acrylonitrile and isobutylene in the reaction scheme of said patent provides a route to unsaturated $C_{10}$ dinitriles which can be hydrogenated to saturated $C_{10}$ diamines. The saturated diamine products have found utility in a number of areas including the preparation of fiber grade polyamides from the reaction of said diamines with terephthalic acid, as disclosed in U.S. Pat. No. 3,980,621 of Robert W. Campbell and H. Wayne Hill, Jr. In addition, U.S. Pat. No. 3,985,786 of C. A. Drake discloses a single-stage process for the preparation of the unsaturated dinitriles (diadduct) by the reaction of unsaturated mononitrile with suitable olefin in the presence of water and the monoadduct reaction product of the nitrile and the olefin.

In the production of diadduct according to the procedures of the above-described patents, it has been found that in the purification of the crude diadduct by fractional distillation a significant portion of the crude diadduct remains as kettle residues or heavies. A conventional method of disposing of organic distillation heavies is to burn the heavies in the process for their fuel value. However, because of the nitrogen content of the heavies in this instance, it is possible that environmental regulations may prevent this method of disposal from being employed at all or at least for very large amounts of the material. It is also obvious that the amount of heavies produced in the production of the unsaturated dinitrile represents a loss of starting olefin and unsaturated mononitrile which is not recovered in the purified unsaturated dinitriles. It has been discovered that significant amounts of the starting materials can be recovered from the diadduct heavies by subjecting the diadduct heavies to pyrolysis conditions to thermally crack at least a portion of the heavies into the starting materials. For example, when isobutylene and acrylonitrile are employed as initial reactants for the production of diadduct comprising unsaturated $C_{10}$ dinitriles, the heavies which can amount to about 30% of the unsaturated dinitrile crude product, can be pyrolyzed to provide recoverable amounts of acrylonitrile and isobutylene as well as lesser amounts of the monoadduct of acrylonitrile with isobutylene. However, a problem has been encountered in the pyrolysis of the diadduct heavies in that the pyrolysis reactor containing particulate heat transfer material can be plugged with a solid material which appears to be essentially all carbon or at least has a very high carbon content. It also appears that the plugging material forms an extremely tight bond to the surfaces of the heat transfer particulate material in the pyrolysis reactor such that the heat transfer material cannot conveniently be freed from the deposited material and must be discarded. It is obvious that this condition represents a serious economic loss in the process in terms of interruption of the desired pyrolysis as well as loss of useful heat transfer surface material which must be replaced in the pyrolysis reactor.

In addition, the diadduct heavies are extremely viscous and must be heated in order to be pumpable or otherwise handled with any degree of ease. Even in the heated condition, the diadduct heavies are extremely viscous and tacky materials which adds to the problem of their handling and ultimate disposal.

According to the instant invention, it has been found that the problem of plugging in the pyrolysis reactor containing particulate heat transfer material and the problem of high viscosity in the diadduct heavies can be alleviated greatly by carrying out a preliminary high temperature distillation of the diadduct heavies prior to charging to a pyrolysis reaction zone containing particulate heat transfer material. It has been found that not only can the pyrolysis reaction be carried out for a longer period of time prior to plugging but that the distilled diadduct heavies which are charged to the pyrolysis zone actually appear to be of lower viscosity than the original diadduct heavies before treatment according to the process of the instant invention.

Accordingly it is an object of the present invention to reduce the amount of heavies which must ultimately be subjected to disposal. Another object of the invention is to recover economically valuable products from the heavies. It is an object of the invention to improve the economic feasibility of a process for the production of unsaturated dinitriles. Yet another object is to improve the yield of desired products. A further object of the invention is to provide a new and improved process for the production of unsaturated dinitriles. Another object of the invention is to minimize plugging of the reactor for the pyrolysis of the diadduct heavies. A further object of the invention is to improve the handling characteristics of the heavies to be pyrolyzed. Other objects, aspects and advantages of the invention will be apparent from a study of the specification, the drawing and the appended claims to the invention.

In accordance with the present invention, the diadduct heavies are subjected to distillation to provide a light cut and a residue or heavy cut and the light cut is then subjected to pyrolysis in a pyrolysis reaction zone containing particulate heat transfer material to thermally crack at least a portion of the light cut heavies into the starting materials and/or other useful materials. The starting materials can be recycled to the diadduct formation process.

The present invention is applicable to both the two-stage process and the single-stage process for the production of the unsaturated dinitriles; however the single-stage process is preferred and the detailed description will be in terms of a single-stage process for the production of diadduct. In the single-stage process, an unsaturated mononitrile, e.g., acrylonitrile, is reacted with an olefinic hydrocarbon compound, e.g., isobutylene, to produce unsaturated mononitriles (monoadduct) having a greater number of carbon atoms, e.g., 5-methyl-5-hexenenitrile. The monoadduct can be recovered and passed to the second stage wherein the unsaturated dinitriles (diadduct), e.g., 5-methylene-nonanedinitrile and 5-methyl-4-nonenedinitrile, are formed by the monoaddition of an unsaturated mononitrile, e.g. acrylonitrile, and a monoadduct reaction product. In the single-stage process, an unsaturated mononitrile and an olefinic hydrocarbon compound are introduced into a reactor, preferably along with monoadduct, to form monoadduct and diadduct in the single reactor. The reaction effluent of the single stage or from the second stage of the two-stage process can be separated into diadduct product, unreacted monoadduct, unreacted unsaturated mononitrile, unreacted olefinic hydrocarbon compound and diadduct heavies. Small amounts of dimers of the unsaturated mononitrile may also be present. The unreacted monoadduct and the unreacted unsaturated mononitrile can be recycled to the appropriate stage. The heavies can be fractionated and the resulting light cut subjected to pyrolysis in accordance with the present invention and the unsaturated mononitrile, olefinic compound, and monoadduct recovered from the pyrolysis effluent can be recycled to the appropriate reaction stage.

In the drawing, the single FIGURE is a diagrammatic illustration of a single-stage reaction process for the production of unsaturated dinitriles which embodies the present invention.

Any unsaturated mononitrile can be employed in the practice of this invention provided the mononitrile contains ethylenic unsaturation, contains at least one hydrogen atom attached to a doubly bonded carbon atom, and contains a cyano group attached to a carbon atom adjacent and doubly bonded to a carbon atom which is attached to at least one hydrogen atom. Preferably the mononitrile reactant is free of acetylenic unsaturation and contains from 1 to 2 ethylenically unsaturated, nonconjugated double bonds as the sole aliphatic unsaturation, while the total number of carbon atoms in the mononitrile reactant is within the range of 3 to 18, more preferably within the range of 3 to 8. Illustrative unsaturated mononitrile reactants include those represented by the formula

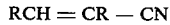

RCH = CR — CN wherein each R is independently selected from the group consisting of hydrogen and hydrocarbyl radicals. Preferably the hydrocarbyl radicals are selected from the group consisting of alkyl, cycloalkyl, and aryl hydrocarbyl radicals and combinations thereof, such as alkylcycloalkyl, cycloalkylalkyl, aralkyl, alkaryl, and arylcycloalkyl radicals. Examples of unsaturated nitriles meeting the requirements of the above formula are acrylonitrile, methacrylonitrile, 2-decenenitrile, 3-cyclohexyl-2-propenenitrile, 4-phenyl-2-butenenitrile, 3(p-tolyl)-2-propenenitrile, 2-butenenitrile, 2-hexenenitrile, 5-methyl-2-hexenenitrile, 4-methyl-2-heptenenitrile, 6,6,8,8-tetramethyl-2-nonenenitrile, 6-cyclohexyl-2-octenenitrile, 6-phenyl-2-decenenitrile, 2-octadecenenitrile, 6,7,8-trimethyl-9-phenyl-2-nonenenitrile, 5-p-tolyl-2-nonenenitrile, and the like, and mixtures of any two or more thereof.

Any acyclic or cyclic olefinic hydrocarbon compound can be employed in the practice of this invention, provided that the compound has at least one olefinic linkage having joined to one of the doubly bonded carbons a carbon atom having at least one hydrogen atom attached thereto. The olefinic hydrocarbons preferably are free of acetylenic unsaturation and have from 3 to 18 carbon atoms per molecule with from 1 to 2 ethylenically unsaturated, nonconjugated double bonds as the sole aliphatic unsaturation. The preferred types of these compounds are the open chain monoolefinic hydrocarbons represented by the formula $R'_2C{=}CR'{-}CHR'_2$, wherein each R' is independently selected from the group consisting of hydrogen and hydrocarbyl radicals, said hydrocarbyl radicals being selected from the group consisting of alkyl, cycloalkyl, and aryl hydrocarbyl radicals and combinations thereof. Especially preferred are those monoolefinic hydrocarbons having 3 to 12 carbon atoms and having an alkyl group, preferably methyl, as a side chain attached to at least one of the carbon atoms comprising the ethylenic linkage. Specific examples of olefinically unsaturated hydrocarbon compounds which are useful in the process of this invention include propylene, isobutylene, diisobutylene, triisobutylene, 1,5-hexadiene, beta-pinene, 1,5-cyclooctadiene, 2,4,4-trimethyl-1-pentene, 2-butene, biallyl, bimethallyl, alpha-methylstyrene, beta-methylstyrene, 1-pentene, 1-decene, cyclohexene, 1-allylcyclohexene, 3-allylcyclohexene, 4-allylcyclohexene, allylbenzene, 3,4,4-trimethyl-2-pentene, 1-dodecene, 2,3-dimethyl-2-butene, and 2-methyl-1-phenyl-2-propene, and the like, and mixtures of any two or more thereof.

Suitable monoadduct reactants include any monoadduct reaction product of an olefinic hydrocarbon as hereinabove defined, and an unsaturated mononitrile, as hereinabove defined. It is believed that the olefinic hydrocarbon compound and the unsaturated mononitrile react in accordance with the "ene" reaction to produce, as the principal monoadduct reaction product, a compound having the structural formula

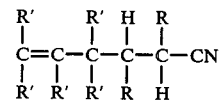

wherein R and R' are as defined hereinabove. Generally a lesser amount of an isomeric monoadduct reaction product having the formula

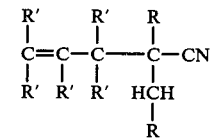

wherein R and R' are as defined hereinabove, is also produced. Thus, isobutylene and acrylonitrile react to produce 5-methyl-5-hexenenitrile as the principal monoadduct reaction product along with a small amount of 2,4-dimethyl-4-pentenenitrile. It can be readily seen that isobutylene as the olefinic hydrocarbon reactant possesses six of the required allylic hydrogens but that all six are structurally equivalent so that only two monoadduct reaction compounds corresponding to the above general formulas are produced according to the "ene" reaction.

However, it will also be evident that if a compound having two or more allylic hydrogens which are not structurally equivalent is employed as the olefinic hydrocarbon reactant, the number of expected isomeric monoadduct reaction product compounds having the above general formulas will be increased. For example, if 2,4,4-trimethyl-1-pentene is reacted with acrylonitrile, the major monoadduct reaction products expected according to the "ene" reaction would be 5-methylene-7,7-dimethyloctanenitrile and 4-methylene-2,6,6-trimethylheptanenitrile with lesser amounts of 5,7,7-trimethyl-5-octenenitrile and 4-t-butyl-5-methyl-5-hexenenitrile. Other factors not fully understood at present may influence the relative amounts of the possible isomers in the monoadduct reaction product. The isomeric mixture reaction product produced by the reaction of an olefinic hydrocarbon and an olefinically unsaturated nitrile can be employed as the monoadduct reactant, or one or more isomers can be separated from the isomeric mixture reaction product and such separated isomer or isomers can be employed as the monoadduct reactant. Examples of suitable monoadduct reactants include 5-methyl-5-hexenenitrile, 3,5-dimethyl-5-hexenenitrile, 3-(n-propyl)-5-hexenenitrile, 3-(n-propyl)-6-phenyl-5-hexenenitrile, 2,4-dimethyl-4-pentanenitrile, 2-ethyl-4-methyl-4-pentenenitrile, 2-(n-butyl)-4-pentenenitrile, 2-(n-butyl)-5-phenyl-4-pentenenitrile, and mixtures of any two or more thereof.

The diadduct reaction products obtained by the process of this invention comprise the reaction product mixtures formed by the monoaddition of an unsaturated mononitrile and any monoadduct reaction product. Exemplary of a diadduct reaction product is the reaction product mixture containing as the major isomer species, 5-methylenenonanedinitrile and 5-methyl-4-nonenedinitrile; and containing the minor isomer species 2-methyl-4-methyleneoctanedinitrile, 2,4-dimethyl-4-octenedinitrile, 2,4-dimethyl-3-octenedinitrile, 2,6-dimethyl-4-methyleneheptanedinitrile and 2,4,6-trimethyl-3-heptenedinitrile.

Any amount of olefinic hydrocarbon, olefinically unsaturated mononitrile and monoadduct reaction product can be employed in the production of the diadduct reaction products. In general the mol ratio of olefinically unsaturated mononitrile reactant to olefinic hydrocarbon reactant will be in the range of about 10:1 to about 0.1:1, preferably in the range of about 5:1 to about 0.2:1, and more preferably in the range of about 2:1 to about 0.3:1. In a single step process the monoadduct reaction product will generally be employed in an amount such that during substantially the entire reaction period the net monoadduct reaction product present in the reaction mixture will constitute from about 10 to about 90, preferably from about 20 to about 80, and more preferably from about 30 to about 70 weight percent of the total reaction mixture. The net amount of monoadduct reaction product present in the reaction zone is the sum of the amount of monoadduct reaction product charged to the reaction zone plus the amount of monoadduct reaction product produced by the reaction of the olefinic hydrocarbon reactant and the olefinically unsaturated mononitrile reactant in the reaction zone less the monoadduct reaction product consumed by reaction with the olefinically unsaturated mononitrile in the reaction zone to produce diadduct. The monoadduct reaction product charged to the reaction zone can be the same as or different from the monoadduct reaction product produced by the reaction of the olefinic hydrocarbon reactant and the olefinically unsaturated mononitrile reactant in the reaction zone, but it will be generally preferred for them to be the same. The total reaction mixture includes all fluid materials present in the reaction zone, i.e., reactants, diluents, products, byproducts, etc.

Any suitable reaction conditions for either a batch process or a continuous process can be employed in the production of the diadduct reaction products. The reaction time employed can vary widely. Generally a time period of from about 2 minutes to about 48 hours, preferably from about 30 minutes to about 10 hours, and more preferably from about 1 hour to about 5 hours is an adequate period of time for olefin, unsaturated mononitrile and a monoadduct reaction product to be suitably admixed in the preparation of reaction products in high yields in a single-stage batch process. In a continuous single-stage process the liquid hourly space velocity will generally be in the range of about 0.05 to about 20, preferably in the range of about 0.1 to about 10, more preferably in the range of about 0.5 to about 2.

The reaction temperatures that can be employed can vary widely. Generally, however, suitable reaction temperatures for the single stage reaction are within the range of about 100° C. to about 500° C., and preferred reaction temperatures are within the range of about 200° C. to about 350° C.

The reaction pressures suited to the practice of this invention also vary widely. Reaction pressures within a range of about atmospheric pressure to about 689.47 MPa (100,000 psig) can be employed in the single stage process; however, reaction pressures within the range of about 3.45 MPa (500 psig) to about 27.58 MPa (4000 psig) are preferably employed.

If desired, the production of the diadduct can be carried out in the presence of a polymerization inhibitor. The use of the inhibitor often advantageously limits side reactions such as the dimerization or polymerization of the olefinically unsaturated mononitrile. When an inhibitor is employed, it is generally desirable that an amount in the range of about 0.001 to about 5, preferably in the range of about 0.1 to about 1, percent by weight inhibitor based on the weight of unsaturated mononitrile reactant be employed. Suitable inhibitors include hydroquinone, 2,6-di-tert-butyl-paracresol, 2,6-di-tert-butylhydroquinone, 4-tert-butylcatechol, para-hydroxydiphenylamine, and the like, and combinations of any two or more thereof.

The reaction of the above described olefinic hydrocarbon reactant, olefinically unsaturated mononitrile reactant and monoadduct reaction product reactant is preferably carried out in the presence of a diluent. While any suitable diluent can be employed, the presently preferred diluent is an aqueous diluent comprising at least 50 weight percent water, more preferably at least 80 weight percent water, and more preferably consisting essentially of water. The codiluent, if employed, can be any solvent or diluent which is nonreactive with either the reactants or the reaction products. Examples of other suitable diluents which can be employed alone or as codiluents include benzene, toluene, para-xylene, ortho-xylene, meta-xylene, ethyl-benzene, diethyl ether, ethyl propyl ether, dibutyl ether, tetrahydrofuran, dioxane, cyclohexane, carbon tetrachloride, methylene chloride, and the like, and mixtures of any two or more thereof.

The diluent can be employed in any suitable amount. In general the diluent will be employed in an amount in the range of about 0.01 to about 40 parts by weight of total diluent per part by weight of olefinically unsaturated mononitrile reactant charged to the reaction zone. The amount of diluent currently preferred is in the range of about 0.1 to about 20 parts by weight of total diluent per part by weight of olefinically unsaturated mononitrile reactant charged to the reaction zone. The advantages of the aqueous diluent system include improved selectivity to the desired olefinically unsaturated dinitrile and reduced amounts of heavy polymeric byproduct. This latter byproduct is particularly objectionable because it tends to foul reactor surfaces.

A convenient method of carrying out this invention comprises heating a mixture of an olefinically unsaturated mononitrile (e.g., acrylonitrile), an olefinic hydrocarbon compound (e.g., isobutylene), and a monoadduct reaction product reactant (e.g., a mixture of 5- methyl-5-hexenenitrile and 2,4-dimethyl-4-pentenenitrile) in a reaction pressure vessel at a temperature within the range of about 240° to about 350° C. and at a pressure in the range of about 3.45 to about 27.58 MPa (about 500 to about 4000 psig); the mol ratio of the olefinically unsaturated mononitrile to the olefinic hydrocarbon being in the range of about 5:1 to about 0.2:1; and the concentration of the monoadduct reaction product reactant in the reaction mixture being in the range of about 20 to about 80 weight percent. Thereafter, the resulting olefinically unsaturated dinitrile reaction product is readily isolated from the reaction effluent mixture by any convenient product recovery method, such as fractional distillation. Any suitable temperatures and pressures can be employed in a single batch fractional distillation zone or in a plurality of fractional distillation zones operated in batch or continuous operation in any desired sequence. However, low temperatures and subatmospheric pressures are desirable to avoid polymerization and/or thermal degradation of the desirable materials. In general the fractional distillation temperatures will be in the range of about 15° to about 350° C., and preferably in the range of about 25° to about 250° C., while the fractional distillation pressures will generally be in the range of about 0.01 kPa to about 110 kPa and preferably will be in the range of about 0.1 kPa to about 100 kPa. The reaction effluent mixture can be readily separated by fractional distillation into a diluent stream, an unreacted olefinically unsaturated mononitrile (e.g., acrylonitrile) stream, an unreacted olefinic hydrocarbon compound (e.g., isobutylene stream), a monoadduct reactant (e.g., a mixture of 5-methyl-5-hexenenitrile and 2,4-dimethyl-4-pentenenitrile) stream, a diadduct (e.g., a mixture of olefinically unsaturated $C_{10}$ dinitriles) stream, and a diadduct heavies stream. The diadduct heavies constitute that portion of the reaction effluent mixture which has a boiling point significantly higher than the diadduct. In the one-step synthesis of diadduct from acrylonitrile, isobutylene and monoadduct of acrylonitrile and isobutylene, the reaction effluent contains isobutylene, acrylonitrile, monoadduct, α-methyleneglutaronitrile, trans-1,2-dicyanocyclobutane, cis-1,2-dicyanocyclobutane, diadduct, and diadduct heavies, listed in the order of increasing boiling points. Isobutylene (boiling point −6° C. at 760 mm) and acrylonitrile (boiling point 78°–79° C. at 760 mm) can be readily separated by simple fractionation and recycled to the diadduct synthesis reaction. Fractional distillation of acrylonitrile at low pressure and temperature is advantageous in minimizing polymerization of the acrylonitrile. Recovery of monoadduct (boiling point of about 120° C. at 125 mm) for recycle can be accomplished by fractional distillation of the monoadduct from the small amounts of α-methyleneglutaronitrile (boiling point 140° C. at 16 mm) and trans-1,2-dicyanocyclobutane (boiling point 122° C. at 6 mm). After removal of the monoadduct and the two light boiling dimers, the resulting kettle product can be introduced into another fractional distillation column for the separation of the diadduct from the heavies. Elaborate fractionation is not required for this latter separation, but relatively low pressure is desirable in order to minimize thermal degradation of the diadduct (boiling point 176° C. at 10 mm, 192° C. at 20 mm). Small amounts of close boiling cis-1,2-dicyanocyclobutane are generally taken overhead with the diadduct, but the products of hydrogenation of this byproduct are readily separated from the diamines obtained by hydrogenation of the diadduct.

In the process employing acrylonitrile, isobutylene and the monoadduct thereof, the diadduct heavies are black-brown, extremely viscous and tacky materials at 23° C., and can be characterized by the observation that approximately 90 weight percent of the heavies are not distillable at 0.0133 kPa and 320° C. A typical sample of the diadduct heavies produced in a process for the production of diadduct from acrylonitrile and isobutylene and the monoadduct thereof showed the following analysis in terms of elemental content: 75.2 weight percent carbon, 8.4 weight percent hydrogen, and 15.7 weight percent nitrogen. Molecular weight analysis indicated an average molecular weight of 629. Infrared anaylsis of the diadduct heavies indicated the presence of a secondary amine function as well as the nitrile functional group. The material also contained a small amount of olefinic unsaturation. Nuclear magnetic resonance (NMR) analysis of the diadduct heavies did not detect any aromatic protons in the material and further indicated that the secondary amine function was evidently a minor component of the material and further confirmed the low concentration of the olefinic unsaturation in the material. Although, on occasions, dimers of acrylonitrile have been recovered, dimers and trimers of isobutylene have not been detected in the diadduct synthesis reaction effluent. The above analyses taken together indicated that the diadduct heavies probably represent an oligomer (tetramer) of the diadduct which had polymerized through the olefinic unsaturation in the diadduct, and small amounts of an oligomer or low molecular weight polymer of acrylonitrile. Since the diadduct itself is a mixture of isomeric unsaturated dinitriles having 10 carbon atoms per molecule, it is very likely that the tetramers are a complex mixture of isomeric materials.

In accordance with the present invention the diadduct heavies are subjected to fractional distillation at elevated temperatures in any suitable fractional distillation equipment to produce a light or overhead cut and a kettle residue or heavy cut. The division between the light cut and the heavy cut can be made at any desired point, but in general the heavy cut will constitute from 3 to 50, preferably from 5 to 40, and more preferably from 8 to 30, weight percent of the total heavies fed to this distillation. The residue appears to be a material of very high carbon content and is believed to be the component in the diadduct heavies which is principally responsible for the plugging of the pyrolysis reactor. The light cut of the diadduct heavies will generally constitute from 50 to 97, preferably from 60 to 95, and more preferably from 70 to 92, weight percent of the total diadduct heavies. The distillation column can be of any suitable type, for example, a packing free single stage still or a packing free multiple stage column. Any suitable temperature and pressure can be employed in the fractionation of the diadduct heavies. However, the temperature will generally be in the range of about 440° to about 650° C., preferably in the range of about 450° to about 620° C., and more preferably in the range of about 500° to about 600° C. The pressure employed in the distillation of the heavies will generally be in the range of about 0.01 to about 110 kPa, preferably in the range of about 0.01 to about 50 kPa, and more preferably in the range of about 0.01 to about 25 kPa. it is desirable that the fractional distillation temperature be sufficiently high to promote light to moderate thermal cracking of the diadduct undergoing fractionation but not so high as to cause severe cracking and coke formation. The resulting distillation overhead can the be passed to the pyrolysis reactor containing particulate heat transfer material for the major cracking operation. The residue from the heavies distillation can be withdrawn and passed to disposal or other point of utilization.

Any suitable temperature, pressure, and reaction time can be employed in the pyrolysis of the light cut of the diadduct heavies. In general the pyrolysis temperature will be in the range of about 450° to about 1000° C., preferably in the range of about 500° to about 900° C., and more preferably in the range of about 550° to about 700° C. The pressure in the pyrolyzing reaction zone will generally be in the range of about 1 kPa to about 1000 kPa, preferably in the range of about 25 kPa to about 200 kPa, and more preferably in the range of about 50 kPa to about 120 kPa. The pyrolysis of the light cut of the diadduct heavies can be conducted as a thermally induced reaction in the absence of any catalytic material. While the pyrolysis can be conducted as a batch reaction for a suitable time, e.g., in the range of about 5 minutes to about 10 hours, it will preferably be as a continuous process. The liquid hourly space velocity (LHSV) for a continuous pyrolysis reaction will generally be in the range of about 0.1 to about 10, preferably in the range of about 0.5 to about 2, volumes of liquid feed per hour per volume of pyrolysis reaction zone.

If desired, an inert gas such as nitrogen, carbon dioxide, helium, argon, and the like, or a mixture thereof, can be passed through the pyrolysis reaction zone in order to effectively sweep the pyrolysis products from the reaction zone to prevent subsequent side reactions of the desired products under the high temperatures employed in the reaction zone. The inert gas stream can be employed at any suitable rate, but will generally be utilized at a gas hourly space velocity (GHSV) in the range of about 1 to about 500, preferably in the range of about 5 to about 100, standard volumes of inert gas per hour per volume of the pyrolysis reaction zone.

As is conventional in most pyrolysis reactions, the process of the present invention preferably employs particulate materials in the pyrolysis reaction zone having a high surface area and an ability to transfer heat from the reaction zone to the feed material. For example, quartz chips, stainless steel chips, refractory oxides of various types including alumina, thoria, titania, and the like, and admixtures of any two or more thereof, can be utilized as the heat transfer material in the pyrolysis reaction zone. Such particulate materials can be in any of a variety of shapes and sizes, such as beads, chips, pellets, shaving, and the like, as well as mixtures of any two or more thereof.

In order to recover the valuable pyrolysis products obtained according to the present invention, the effluent from the pyrolysis reaction zone can be passed to suitable recovery and separation means, e.g., one or more condensation traps or zones maintained at a relatively low temperature can be employed in order to collect the products. If more than one condensation trap or zone is employed, it is possible to maintain different temperatures in the condensation zones in order to selectively condense products from the pyrolysis reaction zone. It is also possible to employ a single condensation zone in order to trap essentially all of the products of the pyrolysis. The material collected in the condensation zone or zones can then be fractionally distilled to separate the products of the pyrolysis into relatively pure streams. For example, in the case of diadduct heavies obtained from acrylonitrile and isobutylene as the starting materials, the fractional distillation of the pyrolysis effluent collected in the condensation zone can result in the recovery of relatively pure streams of each of acrylonitrile, isobutylene, monoadduct and diadduct. It is, of course, possible to recycle the first three materials to the appropriate process steps for the conversion of acrylonitrile and isobutylene into monoadduct and diadduct. It is also possible to recycle any remaining diadduct heavies to the pyrolysis zone for further conversion according to the instant invention, while withdrawing from the process any residue char and/or light gaseous products.

Referring now to the drawing, an embodiment involving a continuous process for the reaction of acrylonitrile, isobutylene and a monoadduct of acrylonitrile and isobutylene to produce 5-methylenenonanedinitrile and 5-methyl-4-nonenedinitrile will be described. Acrylonitrile and isobutylene are introduced into single stage reactor 11 by way of conduit means 12 and 13, respectively. The monoadduct of acrylonitrile and isobutylene, i.e., predominately 5-methyl-5-hexenenitrile with a small amount of 2,4-dimethyl-4-pentenenitrile, is introduced into reactor 11 by way of conduit means 14, while water is introduced into reactor 11 by way of conduit means 15. A convenient method of carrying out the production of the diadduct in reactor 11 comprises heating the mixture of acrylonitrile, isobutylene, and the mixture of 5-methyl-5-hexenenitrile and 2,4-dimethyl-4-pentenenitrile in a reaction pressure vessel at a temperature within the range of about 240° to about 350° C. and at pressures in the range of about 3.45 to about 27.58 MPa (about 500 to about 4000 psig), the mol ratio of the acrylonitrile to the isobutylene being in the range of about 5:1 to about 0.2:1, and the concentration of the monoadduct reactant in the reaction mixture being in the range of about 20 to about 80 weight percent.

The reaction effluent is withdrawn from reactor 11 and passed by way of conduit means 16 to a suitable separation zone 17. A relatively pure diadduct product stream comprising 5-methyl-4-nonenedinitrile and 5-methylenenonanedinitrile and small amounts of other $C_{10}$ olefinically unsaturated dinitriles is withdrawn from separation zone 17 and from the process by way of conduit means 18. A relatively pure monoadduct stream comprising 5-methyl-5-hexenenitrile and 2,4-dimethyl-4-pentenenitrile is withdrawn from separation zone 17 is recycled to reactor 11 by way of conduit means 19 and 14. Similarly an acrylonitrile stream, an isobutylene stream and a water stream are withdrawn from separation zone 17 and passed by way of conduit means 21 and 12, 22 and 13, and 23 and 15, respectively, to reactor 11. The remainder of the reaction effluent from reactor 11 is withdrawn from separation zone 17 by way of conduit means 24 as a diadduct heavies stream and is introduced into fractional distillation zone 25. An overhead product or light cut is withdrawn from fractional distillation zone 25 and passed by way of conduit means 26 to pyrolysis zone 27. The bottoms product or residue is withdrawn from fractional distillation zone 25 and from the process by way of conduit means 28. Pyrolysis zone 27 is filled with non-catalytic high surface area particulate heat transfer material and is heated to a temperature in the range of about 550° to about 700° C. An inert gas is introduced into pyrolysis zone 27 through conduit means 29 to flush the pyrolysis products from zone 27 through outlet conduit means 30, containing cooling means 31, into separation zone 32. A relatively pure diadduct product stream is recovered from separation zone 32 and passed by way of conduit means 33 into conduit means 18. A relatively pure monoadduct stream is recovered from separation zone 32 and passed through conduit means 34 and 14 to reactor 11. An acrylonitrile stream and an isobutylene stream are passed from separation zone 32 through conduit means 35 and 36, respectively, to reactor 11. A stream containing unreacted and/or relatively unreacted heavies can be passed through conduit means 37 from separation zone 32 to pyrolysis zone 27. An off-gas stream comprising inert gas and light gaseous cracked products is withdrawn from separation zone 32 by way of conduit means 38 for disposal or utilization, e.g., as a fuel gas. A residue stream containing carbon, char and very high molecular weight material is withdrawn from separation zone 32 and from the process by way of conduit means 39.

The following examples are presented in further illustration of the invention and should not be construed in undue limitation thereof.

EXAMPLE I

A quartz reactor tube of 1.9 cm outside diameter and 36 cm in length was filled with quartz chips to serve as the pyrolysis reaction zone for diadduct heavies obtained from the reaction of acrylonitrile and isobutylene in the preparation of unsaturated $C_{10}$ dinitriles. A heated dropping funnel with a pressure equalizing tube was mounted directly onto the quartz tube. The diadduct heavies were fed through the funnel onto the quartz chips in the pyrolysis reactor for a period of 1 hour at a temperature of 600° C. An argon sweep through the pyrolysis reaction removed products as they formed. The decomposition products were recovered by the use of a wet ice trap followed by a dry ice trap. A total weight of 26.20 grams of material was recovered in the traps. The feed was briefly interrupted to remove the sample of collected material and then resumed for a period of 1 hour and 50 minutes to collect another sample at 625° operating temperature. The second sample of material weighed 58.41 grams and there was also recovered 3.85 grams of condensed material in the second dry ice trap for a total weight of 62.26 grams. The reaction was terminated because of plugging of the pyrolysis reactor by an insoluble solid black material. After the reactor was taken apart, it was found that the deposited plugging material could not be removed by washing with various solvents and the quartz chips had to be chiseled from the tube and were discarded.

The collected liquid material from the pyrolysis reaction zone was fractionally distilled (58 grams) to recover about 10 grams of material identified as isobutylene and about 11.8 grams of acrylonitrile, about 13 grams of other unidentified materials and about 20 grams of kettle residue.

This control run demonstrates that the pyrolysis, although successful in producing the desired products, acrylonitrile and isobutylene, was terminated after a total reaction time of 2 hours and 50 minutes due to the plugging of the reaction zone.

EXAMPLE II

Another control run was carried out using the same apparatus as that employed in Example I above. In this run the pyrolysis reactor was filled with gamma alumina. However, during the course of the run carried out at about 605° C. for 2 hours, difficulty was experienced in regulating the flow of the feed material to the pyrolysis zone and it was apparent that water was being driven off from the alumina. As a result of these difficulties, the run was terminated with the discarding of the collected material from the pyrolysis reaction zone. The run was then repeated by carrying out a preheating (600° C.) of an alpha alumina material in order to remove water from the alumina in the presence of an argon stream flowing through the system. The pyrolysis of the diadduct heavies was then carried out at a temperature of 610° C. for a period of 1 hour and 40 minutes during which time 51.49 grams of diadduct heavies were fed through the pyrolysis reaction zone. The collected liquid sample weighed 23.3 grams and an additional 3.68 grams was recovered in the secondary cold trap. After about 1 hour and 20 minutes during the run, there was evidence that the reactor was plugging and at 1 hour and 40 minutes the plugging of the reaction zone appeared to be complete and the reaction was terminated. At the termination of the run, it was determined that about 14.7 grams of the diadduct heavies were present in the pyrolysis reactor which further indicated that about 9.8 grams of the diadduct heavies were lost (unaccounted for) during the course of this run.

The results of this run again demonstrate the problem with plugging of the pyrolysis reaction zone that can hinder the efficient use of pyrolysis for obtaining useful products such as acrylonitrile and isobutylene from the diadduct heavies.

EXAMPLE III

A high temperature distillation of diadduct heavies was carried out under carefully controlled conditions by charging 351 grams of the diadduct heavies to a 1-liter distillation flask joined to a second 1-liter receiver by a short U-tube vacuum adapter. The received was maintained at about 0° C. in an ice bath. The temperature for the distillation ranged from 450° to 595° C. at a pressure which ranged from 0.4 to 2 millimeters of mercury (0.053 to 0.266 kPa). There was recovered a light cut of 260 grams of distilled diadduct heavies with a kettle residue of 32 grams and an indicated loss of about 60 grams of diadduct heavies probably in very light material to the vacuum system.

The above described light cut of diadduct heavies was utilized in the pyrolysis reaction system described in Example I. In this pyrolysis run, there was utilized 62.49 grams of the light cut of diadduct heavies at a temperature of 610° C. and at atmospheric pressure with a stream of argon flowing through the system. The reaction was conducted for a period of one hour and no sign of reactor plugging was observed during this period. However, examination of the pyrolysis reactor at the conclusion of the run indicated a gain of 1.47 grams in the reactor. It was also noted that the light cut of diadduct heavies was noticeably less viscous than the diadduct heavies prior to the distillation step. There was a loss of 2.69 grams of the light cut of diadduct heavies in the pyrolysis run which could not be accounted for in the reactor weight gain or the sample weight collected in the cold traps for effluent from the pyrolysis reaction zone. The primary cold trap collected 55.9 grams of material from the pyrolysis reaction zone while the secondary cold trap contained 2.43 grams of effluent from the pyrolysis.

A portion (44.2 grams) of the recovered product from the pyrolysis reaction zone was fractionally distilled through a 6-inch silvered vacuum jacketed Vigreaux distillation column. Table I presents the results of the fractional distillation.

TABLE I

| Cut No. | Temp. ° C. | Pressure kPa | Weight g |
|---|---|---|---|
| 1 | 69 – 81 | 101.3 | 3.75 |
| 2 | 81 –96 | ~101.3 | 6.68 |
| 3 | 96 – 141 | ~101.3 | 4.75 |
| 4 | 32 – 125 | 0.107 | 3.2 |
| 5 | 125 – 183 | 0.107 | 4.16 |
| 6 | 183 – 235 | 0.107 | 5.72 |
| 7 K | — | — | 7.6 |
| Trap | — | — | 5.4 |

Cuts 1, 2 and trap material are principally isobutylene and acrylonitrile. Cuts 1 through 6 are lower boiling than the light cut of diadduct heavies.

Although this run was conducted for only one hour, examination of the pyrolysis reaction zone indicated that a pyrolysis reaction time of greater than 3 hours could have been utilized in this run.

EXAMPLE IV

Another pyrolysis run was carried out utilizing the light cut of diadduct heavies prepared by the distillation described in Example III above. The same pyrolysis reaction system was employed in the instant run as that previously utilized in Example I above. The pyrolysis was carried out under atmospheric pressure at a temperature of 605° C. with a stream of argon flowing through the system. The reaction was conducted for 1 hour and 25 minutes for the collection of the first sample of 67.04 grams of effluent in the first wet ice trap and 7.05 grams in the secondary dry ice trap. The amount of diadduct heavies passed through the pyrolysis reaction zone in this first period was 74.7 grams. After an interruption of 1 hour and 35 minutes duration, the reaction was resumed for an additional one hour. The feed utilized during this latter portion of the reaction period was 18.7 grams and there was collected in the first wet ice trap 7.73 grams of pyrolysis effluent with none being obtained in the secondary dry ice trap. At the end of the latter one hour reaction period, the system was shut down due to a plug formation in the pyrolysis reaction zone. The reactor weight gain during the course of this run was 2.65 grams and there was a loss of 7.07 grams of the feed during the pyrolysis. Although the reaction in this run was terminated due to plugging in the pyrolysis reaction zone, examination of the reactor indicated that the plugging in the current run was much less severe than that observed in Example I above.

Although the pyrolysis reaction effluent was not analyzed in the instant run, it is believed that the effluent collected comprises acrylonitrile and isobutylene as in the previous pyrolysis runs.

Reasonable variations and modifications are possible within the scope of the foregoing disclosure, the drawing and the appended claims to the invention.

I claim:

1. A process which comprises reacting (a) at least one olefinically unsaturated mononitrile reactant and (b) at least one monoadduct of an olefinic hydrocarbon compound and an olefinically unsaturated mononitrile compound under reaction conditions suitable to produce at least one desired olefinically unsaturated dinitrile product and undesired compounds having higher boiling points than said at least one desired olefinically unsaturated dinitrile product, each of said olefinically unsaturated mononitrile reactant and said olefinically unsaturated mononitrile compound containing a cyano group attached to a carbon atom adjacent and doubly bonded to a carbon atom which is attached to at least one hydrogen atom, said olefinic hydrocarbon compound having at least one olefinic linkage having joined to one of the doubly bonded carbons thereof a carbon atom having at least one hydrogen atom attached thereto;

separating the resulting reaction effluent to produce a first fraction comprising said at least one desired olefinically unsaturated dinitrile product and a second fraction comprising said undesired compounds;

distilling said second fraction to produce a light cut and a heavy cut thereof;

subjecting said light cut to pyrolysis conditions in a pyrolysis reaction zone containing particulate heat transfer material to decompose at least a portion of the undesired compounds contained therein to thereby produce a decomposition product comprising at least one of said at least one olefinically unsaturated mononitrile reactant, said at least one monoadduct, said olefinic hydrocarbon compound and said olefinically unsaturated mononitrile compound; and recovering said decomposition product from the resulting pyrolysis effluent.

2. A process in accordance with claim 1 wherein said light cut constitutes from 50 to 97 weight percent of said undesired compounds in said second fraction.

3. A process in accordance with claim 2 wherein said undesired compounds comprise oligomers of the reaction product of said monoadduct and said olefinically unsaturated mononitrile reactant.

4. A process in accordance with claim 3 wherein said pyrolysis conditions comprise a temperature in the range of about 450° to about 1000° C.

5. A process in accordance with claim 4 wherein said pyrolysis conditions further comprise a pressure in the range of about 1 kPa to about 1000 kPa.

6. A process in accordance with claim 5 wherein said pyrolysis conditions further comprise a reaction time in the range of about 5 minutes to about 10 hours for a batch pyrolysis reaction or a liquid hourly space velocity in the range of about 0.1 to about 10 for a continuous pyrolysis reaction.

7. A process in accordance with claim 6 further comprising recycling at least a portion of the thus recovered decomposition product to the step of reacting said at least one olefinically unsaturated mononitrile reactant with said monoadduct.

8. A process in accordance with claim 7 wherein said mononitrile reactant is acrylonitrile, said mononitrile compound is acrylonitrile and said olefinic hydrocarbon compound is isobutylene.

9. A process in accordance with claim 8 wherein said light cut comprises 60 to 95 weight percent of said undesired compounds in said second fraction.

10. A process in accordance with claim 1 further comprising recycling at least a portion of the thus recovered decomposition product to the step of reacting said at least one olefinically unsaturated mononitrile reactant with said monoadduct.

11. A process in accordance with claim 10 wherein said pyrolysis conditions comprise a temperature in the range of about 450° to about 1000° C., a pressure in the range of about 1 kPa to about 1000 kPa, and a reaction time in the range of about 5 minutes to about 10 hours for a batch pyrolysis reaction or a liquid hourly space velocity in the range of about 0.1 to about 10 for a continuous pyrolysis reaction.

12. A process in accordance with claim 11 wherein said light cut comprises 70 to 92 weight percent of said undesired compounds in said second fraction.

13. A process in accordance with claim 1 wherein said pyrolysis reaction conditions comprise a temperature in the range of about 500° to about 900° C. and a pressure in the range of about 25 kPa to about 200 kPa.

14. A process in accordance with claim 1 wherein said mononitrile reactant is acrylonitrile, said mononitrile compound is acrylonitrile, and said olefinic hydrocarbon compound is isobutylene.

15. A process in accordance with claim 14 wherein acrylonitrile and said monoadduct are recovered from said pyrolysis effluent and recycled to the step of reacting acrylonitrile and monoadduct.

16. A process in accordance with claim 1 wherein each of said at least one olefinic hydrocarbon compound, said at least one olefinically unsaturated mononitrile reactant and said at least one olefinically unsaturated mononitrile compound is free of acetylenic unsaturation and has from 3 to 18 carbon atoms per molecule with from 1 to 2 ethylenically unsaturated, nonconjugated double bonds as the sole aliphatic unsaturation.

17. A process in accordance with claim 16 wherein each said olefinic hydrocarbon compound is represented by the formula $R'_2C=CR'—CHR'_2$, wherein each $R'$ is independently selected from the group consisting of hydrogen and hydrocarbyl radicals; and wherein each of said at least one olefinically unsaturated mononitrile reactant and said olefinically unsaturated mononitrile compound is represented by the formula $RCH=CR—CN$ wherein each $R$ is independently selected from the group consisting of hydrogen and hydrocarbyl radicals.

18. A process in accordance with claim 17 wherein said decomposition product comprises said mononitrile reactant and said monoadduct and wherein the mononitrile reactant and monoadduct recovered from said pyrolysis effluent is recycled to the step of reacting said mononitrile reactant with said monoadduct.

19. A process in accordance with claim 18 wherein said decomposition product also comprises said olefinic hydrocarbon compound and further comprising reacting said mononitrile compound with said olefinic hydrocarbon compound to produce monoadduct utilized in said step of reacting said mononitrile reactant with said monoadduct, and recycling the olefinic hydrocarbon compound recovered from said pyrolysis effluent to the step of reacting said mononitrile compound with said olefinic hydrocarbon compound.

20. A process in accordance with claim 19 wherein said light cut comprises 60 to 95 weight percent of said undesired compounds in said second fraction.

21. A process in accordance with claim 1 wherein at least about 90 weight percent of said undesired compounds is not distillable at 0.0133 kPa and 320° C.

22. A process of recovering desirable materials from the heavies fraction of the crude reaction product which has been produced by reacting (a) at least one olefinically unsaturated mononitrile reactant and (b) at least one monoadduct of an olefinic hydrocarbon compound and an olefinically unsaturated mononitrile compound under reaction conditions suitable to produce at least one desired olefinically unsaturated dinitrile product and undesired compounds having higher boiling points than said at least one desired olefinically unsaturated dinitrile product, each of said olefinically unsaturated mononitrile reactant and said olefinically unsaturated mononitrile compound containing a cyano group attached to a carbon atom adjacent and doubly bonded to a carbon atom which is attached to at least one hydrogen atom, said olefinic hydrocarbon compound having at least one olefinic linkage having joined to one of the doubly bonded carbons thereof a carbon atom having at least one hydrogen atom attached thereto; the resulting crude reaction product having been separated into a first fraction comprising said at least one desired olefinically unsaturated dinitrile product and a heavies fraction comprising said undesired compounds; which comprises subjecting said heavies fraction to fractional distillation to produce a heavy cut and a light cut thereof, subjecting said light cut to pyrolysis conditions to decompose at least a portion of the undesired compounds contained therein to thereby produce a decomposition product comprising at least one of said at least one olefinically unsaturated mononitrile reactant, said at least one monoadduct, said olefinic hydrocarbon compound and said olefinically unsaturated mononitrile compound; and recovering said decomposition product from the resulting pyrolysis effluent.

23. A process in accordance with claim 22 wherein said light cut comprises 60 to 95 weight percent of said undesired compounds in said second fraction.

24. A process in accordance with claim 23 wherein said pyrolysis conditions comprise a temperature in the range of about 450° to about 1000° C., a pressure in the range of about 1 kPa to about 1000 kPa, and a reaction time in the range of about 5 minutes to about 10 hours for a batch pyrolysis reaction or a liquid hourly space velocity in the range of about 0.1 to about 10 for a continuous pyrolysis reaction.

25. A process in accordance with claim 24 wherein said mononitrile reactant is acrylonitrile, said mononitrile compound is acrylonitrile and said olefinic hydrocarbon is isobutylene.

26. A process in accordance with claim 17 wherein said reaction conditions comprise a reaction temperature in the range of about 100° C. to about 500° C., a reaction pressure in the range of about atmosphereic pressure to 100,000 psig; and a reaction time in the range of about 2 minutes to about 48 hours for a batch reaction or a liquid hourly space velocity in the range of about 0.05 to about 20 for a continuous reaction.

27. A process in accordance with claim 26 wherein said pyrolysis conditions comprise a temperature in the range of about 450° to about 1000° C., a pressure in the range of about 1 kPa to about 1000 kPa, and a reaction time in the range of about 5 minutes to about 10 hours for a batch pyrolysis reaction or a liquid hourly space velocity in the range of about 0.1 to about 10 for a continuous pyrolysis reaction.

28. A process in accordance with claim 27 wherein said step of separating the resulting reaction effluent is conducted at temperatures in the range of about 15 to about 350° C. and at pressures in the range of about 0.01 kPa to about 110 kPa.

29. A process in accordance with claim 28 wherein said step of distilling said second fraction is conducted at temperatures in the range of about 400° to about 650° C. and at pressures in the range of about 0.01 kPa to about 110 kPa.

30. A process in accordance with claim 29 wherein said light cut constitutes from about 50 to about 97 weight percent of said undesired compounds in said second fraction.

31. A process in accordance with claim 30 wherin said mononitrile reactant is acrylonitrile, said mononitrile compound is acrylonitrile and said olefinic hydrocarbon compound is isobutylene.

* * * * *